(12) United States Patent
Bede et al.

(10) Patent No.: US 6,599,233 B1
(45) Date of Patent: Jul. 29, 2003

(54) RADIOACTIVE SEED HANDLING DEVICE

(75) Inventors: Jessica Bede, New York, NY (US); Mary Anne Dell, Pittsburgh, PA (US); Charles Thiele, Butler, PA (US)

(73) Assignee: Capintec, Inc., Ramsey, NJ (US)

( * ) Notice: Subject to any disclaimer, the term of this patent is extended or adjusted under 35 U.S.C. 154(b) by 0 days.

(21) Appl. No.: 10/090,462

(22) Filed: Mar. 4, 2002

(51) Int. Cl.⁷ .................................................. A61N 5/00
(52) U.S. Cl. .......................................................... 600/7
(58) Field of Search ......................................... 600/1–8

(56) References Cited

U.S. PATENT DOCUMENTS 5,906,574 A * 5/1999 Kan ............................... 600/7
6,113,529 A 9/2000 Shi

* cited by examiner

*Primary Examiner*—John P. Lacyk
(74) *Attorney, Agent, or Firm*—Martin Fleit; Paul D. Bianco; Fleit Kain Gibbons Gutman & Bongini P.L.

(57) ABSTRACT

A radioactive seed handling device for handling a number of radioactive seeds. The device includes a first tubular section having a first lumen with a first diameter larger than the seed diameter for receiving the seed and a second tubular section coupled to the first tubular section and having a second lumen with a second diameter smaller than the seed diameter for preventing seeds from entering the second lumen. An overlapping portion of the second tubular section is located within the first lumen of the first tubular section and has a vent that allows fluid flow into the second lumen when a seed is obstructing a distal end of the second tubular section. The device can be used, for example, in a system to load the seeds into an implant for delivery of radiation in or around cancerous growths.

20 Claims, 1 Drawing Sheet

RADIOACTIVE SEED HANDLING DEVICE

FIELD OF THE INVENTION

The present invention relates to a radioactive seed handling device for manipulating radioactive seeds and to a system using the device to load the seeds into an implant or needle for delivery of radiation in or around cancerous growths.

BACKGROUND OF THE INVENTION

As a result of the continued widespread application of so-called "seeds", i.e. small pellets of low level radioactive material, to deliver localized radiation in the treatment of cancerous growths, a number of systems for handling the seeds have been developed. For example, U.S. Pat. No. 6,113,529 ("the '529 patent") discloses a radioactive seed handling station. Because the seeds are typically inserted in the body via an implant, such as a needle, one critical component of any seed handling system is the mechanism in which the seeds, either alone or in conjunction with non-radioactive spacers, are placed into the needle or other carrier.

Vacuum powered suction is one commonly used mechanism. For example, the '529 patent discloses a vacuum powered seed handling wand that includes a stop for keeping the seeds within a sterile portion of the wand. In one embodiment, the stop is a material such as mesh and fibers. Placing and using such a material in the wand can be problematic and increases the manufacturing time and expense. In another embodiment, the stop is a narrowed portion the lumen of the wand. Although such a mechanism is effective in limiting the movement of the seeds within the wand, the abutment of a seed against the narrowed portion eliminates or reduces airflow, thereby preventing subsequent seeds from being drawn into the wand.

Thus, a need exists for an improved radioactive seed handling device.

SUMMARY OF THE INVENTION

The present invention relates to a radioactive seed handling device for handling a number of radioactive seeds. The device a first tubular section having a first lumen with a first diameter larger than the seed diameter for receiving the seed and a second tubular section coupled to the first tubular section and having a second lumen with a second diameter smaller than the seed diameter for preventing seeds from entering the second lumen. An overlapping portion of the second tubular section is located within the first lumen of the first tubular section and has a vent that allows fluid flow into the second lumen when a seed is obstructing a distal end of the second tubular section.

In one embodiment, the vent is a slit formed on the distal end of the second tubular section. In another embodiment, the distal end of the second tubular section is beveled and the vent is formed by a space created by the beveled end. In another embodiment, the vent is a notch formed in the second tubular section at a distance from the distal end of the second tubular section.

The first tubular section can be made of a material that allows visualization of seeds locating in the first lumen. One such material is glass. The glass can be treated with a shatter resistant protective coating.

In an exemplary embodiment, the first tubular section has a beveled tip. The distal portion of the second tubular section is angled with respect to a proximal portion of the second tubular section and the angle is between about 125 and 145 degrees. In order to provide a fluid-tight seal between the first and second tubular sections, the device can include a connecting tube located between the first and second tubular sections. An example of such a connecting tube is a shrink tube that contracts when heated.

The prevent invention also relates to a radioactive seed handling system. The system includes the radioactive handling device, a vacuum source for generating a vacuum, and a conduit connecting the radioactive seed handling device to the vacuum source. The conduit can include a wand having a handle and a bypass for controlling the vacuum.

BRIEF DESCRIPTION OF THE DRAWINGS

Preferred features of the present invention are disclosed in the accompanying drawings, wherein similar reference numerals denote similar elements throughout the several views, and wherein.

DETAILED DESCRIPTION OF THE INVENTION

In the description that follows, the term "proximal" refers to the end that is closer to the user of the device and the term "distal" refers to the end that is further from the user. Such terms, as well as any reference to direction or orientation are used for convenience of description and are not intended in any way to limit the scope of the invention.

Figure 1:
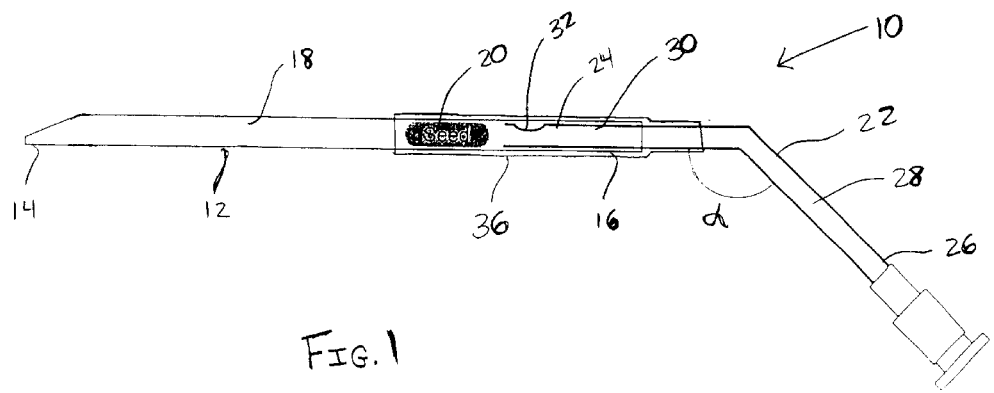
FIG. 1 is a side view of the radioactive seed handling device according to the present invention.

FIG. 1 shows a radioactive seed handling device 10 according to the present invention. Device 10 includes a first tubular section 12 having distal 14 and proximal 16 ends with a lumen 18 extending therebetween. Lumen 18 has a diameter that is larger than the seed diameter so that seeds 20 can be received in distal end 14 and move within lumen 18. Distal end 14 is shown as including a beveled tip, which can facilitate handling of seeds 20 by angling the pick-up mechanism with respect to the tabletop. However, any suitable shape can be used for distal end 14.

Device 10 also includes a second tubular section 22 having distal 24 and proximal 26 ends with a lumen 28 extending therebetween. Proximal end can be provided with a fitting or other coupler for connecting device 10, either directly or indirectly to a vacuum source. Lumen 28 has a diameter that is smaller than the seed diameter, thereby preventing seeds 20 from entering lumen 28. To improve the ergonomics of using device 10, a distal portion of second tubular section 22 can be angled with respect to a proximal portion, with the angle a between about 125 and 145 degrees.

Second tubular section 22 is coupled to first tubular section 12 by an overlapping portion 30. Overlapping portion 30 is located within first lumen 18 and includes a vent 32 that provides a pathway for fluid flow into second lumen 28. As a result, even if a seed 20 is obstructing distal end 24 of second tubular section 22, vent 32 allows fluid flow through second lumen 28.

Figures 2, 3, 4:
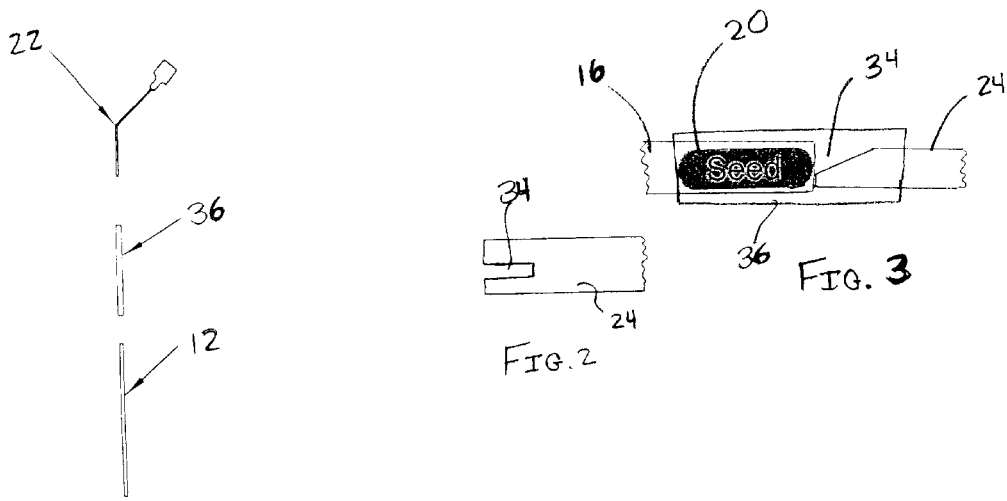
FIG. 2 is a side view of another embodiment of a portion of the radioactive seed handling device.
FIG. 3 is a side view of another embodiment of the region shown in FIG. 2.
FIG. 4 is an exploded view of the radioactive seed handling device shown in FIG. 1.

FIG. 1 shows vent 32 as a notch (created, for example, by machining or filing) formed in second tubular section 22 at a distance from distal end 24. FIG. 2 shows vent 32 as a slit 34 (or group of slits) formed on distal end 24 of second tubular section 22. In FIG. 3, distal end 24 of second tubular section 22 is beveled so that the vent is formed as a space 34 created between the beveled end and seed 20. These non-limiting examples illustrate that vent 32 can be any suitable channel, aperture, opening, or the like that creates an alternative pathway for fluid flow when distal end 24 of second tubular section 22 is blocked.

First tubular member 12 can be made of a material that allows visualization of seeds locating in first lumen 18. The visualization allows the user to aspirate seeds and spacers in the desired order, verify the order, and then release the seeds and spacers. Markings or other indicia may be provided on first tubular member 12 to aid the user in counting seeds and/or spacers therein. If glass or another material that may shatter is used for first tubular member 12, second tubular section 22 can be provided with a shatter resistant protective coating, such as MYLAR.

As a sufficient vacuum must be pulled through device 10, a fluid-tight seal exists between first 18 and second 28 lumens. In an exemplary embodiment, such a seal can be created with a connecting tube 36 located between first 12 and second 22 tubular sections. Connecting tube 36 can be a shrink tube that contracts when heated. Thus, as shown in FIG. 4, device 10 can be made of three separate components that are assembled as follows. One end of connecting tube 36 is slid onto first tubular section 12 and the other end is slid onto second tubular section 22 (after vent 32 has been formed in second tubular section 22). Heat is applied to connecting tube 36 so that connecting tube 36 contracts to form fluid-tight seals between first 12 and second 22 tubular sections.

Figure 5:
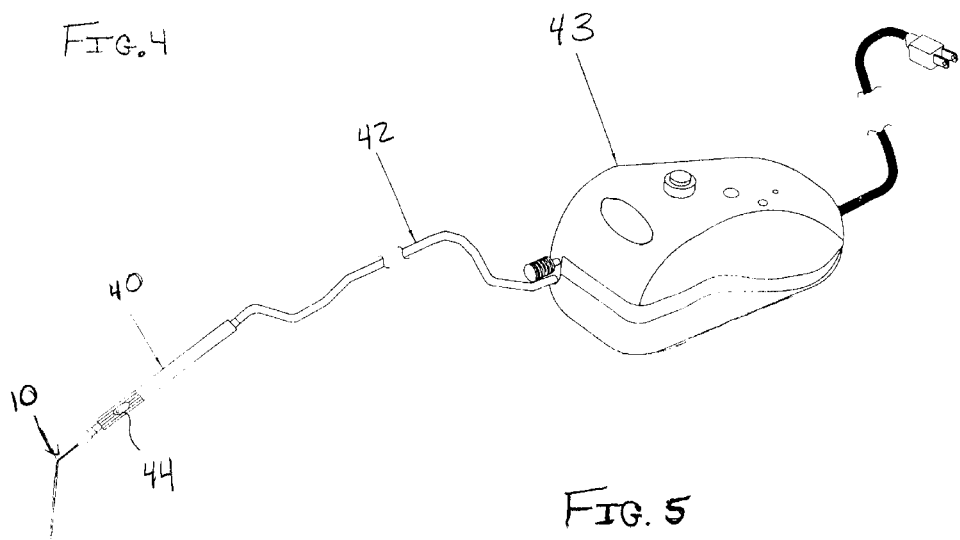
FIG. 5 shows a radioactive seed handling system using the radioactive seed handling device of FIG. 1.

As previously noted, device 10 can be used as part of a radioactive seed handling system. FIG. 5 shows that device 10 is connected to handle 40. Handle 40 has a conduit therein, with one end of the conduit in fluid communication with second lumen 28 and the other end in fluid communication with a vacuum source tubing 42. An opening 44 is provided in handle 40 and is in fluid communication with the handle conduit to serve as a bypass. As a result, air drawn in through tubing 42 will come into the handle conduit through opening 44. If opening 44 is blocked, such as by the user's finger, then air will be drawn through device 10 to allow aspiration of seeds and/or spacers.

In aspirating the first seed or spacer, the seed will freely travel through first lumen 18 until the seed abuts distal end 24 of second lumen 28, which has a smaller diameter than the seed. Vent 32 allows additional seeds and spacers to be aspirated by providing an alternate fluid pathway through second lumen 28 even with the obstruction of distal end 24 by the first seed. This allows the user to aspirate a series of seeds and/or spacers and then visually confirm what has been picked up by looking through first tubular member 12 to verify number, type, and order.

While various descriptions of the present invention are described above, it should be understood that the various features could be used singly or in any combination thereof. Therefore, this invention is not to be limited to only the specifically preferred embodiments depicted herein.

Further, it should be understood that variations and modifications within the spirit and scope of the invention might occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A radioactive seed handling device for handling a number of radioactive seeds each having a seed diameter, the device comprising:

a first tubular section having a first lumen with a first diameter larger than the seed diameter for receiving the seed;

a second tubular section coupled to the first tubular section and having a second lumen with a second diameter smaller than the seed diameter for preventing seeds from entering the second lumen, wherein an overlapping portion of the second tubular section is located within the first lumen of the first tubular section and has a vent that allows fluid flow into the second lumen when a seed is obstructing a distal end of the second tubular section.

2. The radioactive seed handling device of claim 1 wherein the vent is a slit formed on the distal end of the second tubular section.

3. The radioactive seed handling device of claim 1 wherein the distal end of the second tubular section is beveled and the vent is formed by a space created by the beveled end.

4. The radioactive seed handling device of claim 1 wherein the vent is a notch formed in the second tubular section at a distance from the distal end of the second tubular section.

5. The radioactive seed handling device of claim 1 wherein the first tubular section is made of a material that allows visualization of seeds locating in the first lumen.

6. The radioactive seed handling device of claim 5 wherein the first tubular section is made of glass.

7. The radioactive seed handling device of claim 6 wherein the glass has a shatter resistant protective coating.

8. The radioactive seed handling device of claim 1 wherein the first tubular section has a beveled tip.

9. The radioactive seed handling device of claim 1 wherein a distal portion of the second tubular section is angled with respect to a proximal portion of the second tubular section and the angle is between about 125 and 145 degrees.

10. The radioactive seed handling device of claim 1 further comprising a connecting tube providing a fluid-tight seal between the first and second tubular sections.

11. The radioactive seed handling device of claim 10 wherein the connecting tube is a shrink tube that contracts when heated.

12. A radioactive seed handling device for handling a number of radioactive seeds each having a seed diameter, the device comprising:

a first tubular section having proximal and distal ends and a first lumen with a first diameter larger than the seed diameter for receiving the seed;

a second tubular section having proximal and distal ends and a second lumen with a second diameter smaller than the seed diameter for preventing seeds from entering the second lumen; and a connecting tube providing a fluid-tight seal between the proximal end of the first tubular section and the distal end of the second tubular section, wherein an overlapping portion of the second tubular section is located within the first lumen of the first tubular section and has a notch formed at a distance from the distal end of the second tubular section allowing fluid flow into the second lumen when a seed is obstructing the distal end of the second tubular section.

13. The radioactive seed handling device of claim 12 wherein the first tubular section is made of a material that allows visualization of seeds locating in the first lumen.

14. The radioactive seed handling device of claim 13 wherein the first tubular section is made of glass.

15. The radioactive seed handling device of claim 14 wherein the glass has a shatter resistant protective coating.

16. The radioactive seed handling device of claim 12 wherein the first tubular section has a beveled tip.

17. The radioactive seed handling device of claim 12 wherein a distal portion of the second tubular section is angled with respect to a proximal portion of the second tubular section and the angle is between about 125 and 145 degrees.

18. The radioactive seed handling device of claim 12 wherein the connecting tube is a shrink tube that contracts when heated.

19. A radioactive seed handling system comprising:
   the radioactive seed handling device of claim 12;
   a vacuum source for generating a vacuum; and
   a conduit connecting the radioactive seed handling device to the vacuum source.

20. The radioactive seed handling system of claim 19 wherein the conduit includes a wand having a handle and a bypass for controlling the vacuum.

* * * * *